US00PP37707P2

(12) United States Plant Patent
Rietberg

(10) Patent No.: US PP37,707 P2
(45) Date of Patent: Sep. 22, 2026

(54) ***CHAMAECYPARIS* PLANT NAMED 'El Paso'**

(50) Latin Name: *Chamaecyparis thyoides*
Varietal Denomination: El Paso

(71) Applicant: Henrik Christiaan Cozijn Rietberg, Wezep (NL)

(72) Inventor: Henrik Christiaan Cozijn Rietberg, Wezep (NL)

(73) Assignee: EDENS CREATIONS BV, Wezep (NL)

( * ) Notice: Subject to any disclaimer, the term of this patent is extended or adjusted under 35 U.S.C. 154(b) by 0 days.

(21) Appl. No.: 19/414,261

(22) Filed: Dec. 9, 2025

(30) Foreign Application Priority Data

Aug. 6, 2025 (QZ) ..... 20251763

(51) Int. Cl.
*A01H 7/00* (2006.01)

(52) U.S. Cl.
USPC ..... Plt./213

(58) Field of Classification Search
USPC ..... Plt./213
CPC ..... A01H 7/00
See application file for complete search history.

*Primary Examiner* — Keith O. Robinson
(74) *Attorney, Agent, or Firm* — Penny J. Aguirre

(57) ABSTRACT

A new cultivar of *Chamaecyparis thyoides* plant named 'El Paso' that is characterized by its unique, distinctive foliage that is cactus-like in appearance, its sturdy leaf texture, its cold hardiness at least to U.S.D.A. Zone 6, its sun tolerance, and its strong adaptability to a wide range of environmental conditions, including cold, wet, warm, and dry climates.

2 Drawing Sheets

Botanical classification: *Chamaecyparis thyoides*.
Varietal denomination: 'El Paso'.

CROSS REFERENCE TO A RELATED APPLICATION

This application is related to a European plant breeders' rights application filed on Aug. 6, 2025, application No. 2025/1763. The Applicant received the information for the Plant breeders' rights application directly from the Inventor.

BACKGROUND OF THE INVENTION

The present invention relates to a new and distinct cultivar of *Chamaecyparis thyoides* and will be referred to hereafter by its cultivar name, 'El Paso'. 'El Paso' represents a new evergreen coniferous shrub grown for landscape use.

The Inventor discovered the new cultivar in spring of 2020 as a naturally occurring branch mutation of *Chamaecyparis thyoides* 'Alpica' (not patented) that was growing in a container in a production greenhouse in Wezep, The Netherlands.

Asexual propagation of the new cultivar was first accomplished by softwood stem cuttings by the Inventor in Wezep, The Netherlands in August of 2020. Asexual propagation by softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'El Paso' as a unique cultivar of *Chamaecyparis*.

1. 'El Paso' exhibits unique, distinctive foliage that is cactus-like in appearance.
2. 'El Paso' exhibits a sturdy leaf texture.
3. 'El Paso' exhibits hardiness at least to U.S.D.A. Zone 6.
4. 'El Paso' exhibits sun tolerance.
5. 'El Paso' exhibits a strong adaptability to a wide range of environmental conditions, including cold, wet, warm, and dry climates.

The parent plant of 'El Paso' differs from 'El Paso' in having a more pyramidal plant habit, less dense foliage that lacks a cactus-like appearance, and a much faster growth rate. 'El Paso' can be most closely compared to *Chamaecyparis* cultivars 'Red Star' (not patented) and 'Heatherbun' (not patented). Both 'Red Star' and 'Heatherbun' are similar to 'El Paso' in leaf structure. 'Red Star' differs from 'El Paso' in having less dense foliage, young foliage has a red hue, and a narrow columnar plant habit. 'Heatherbun' differs from 'El Paso' in having less dense foliage, a looser growth habit, and deeper purple colored foliage in winter.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Mr. Plant Geek (Michael Perry) and Eden Plants & Creations (Instagram and facebook).

BRIEF DESCRIPTION OF THE DRAWINGS

The accompanying color photographs illustrate the overall appearance and distinct characteristics of the new

*Chamaecyparis*. The photographs were taken of a 36-month-old plant of 'El Paso' as grown outdoors in an unheated greenhouse in a 15-cm container in Wezep, The Netherlands.

Figure 1:
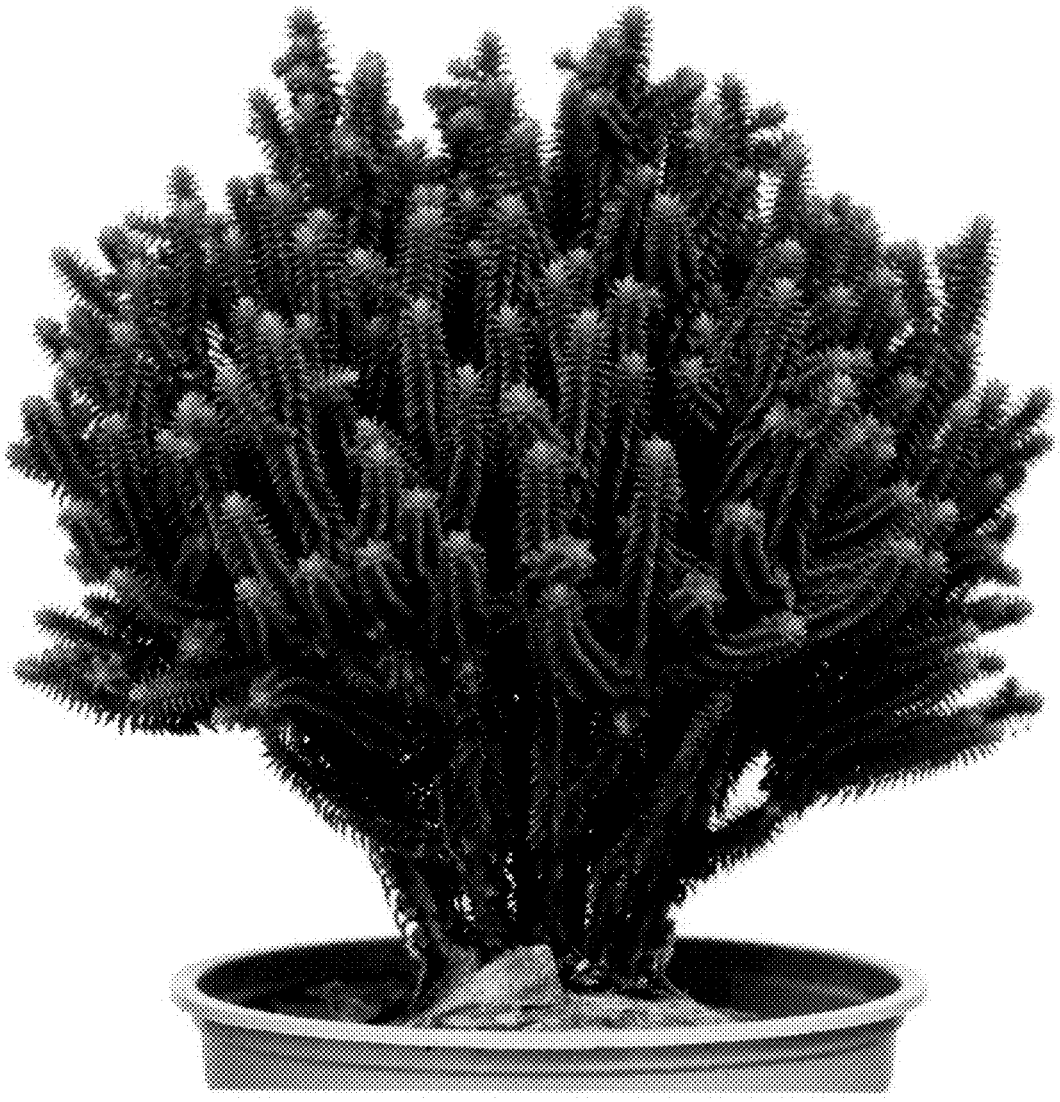

The photograph in FIG. 1 provides a side view of 'El Paso'.

Figure 2:
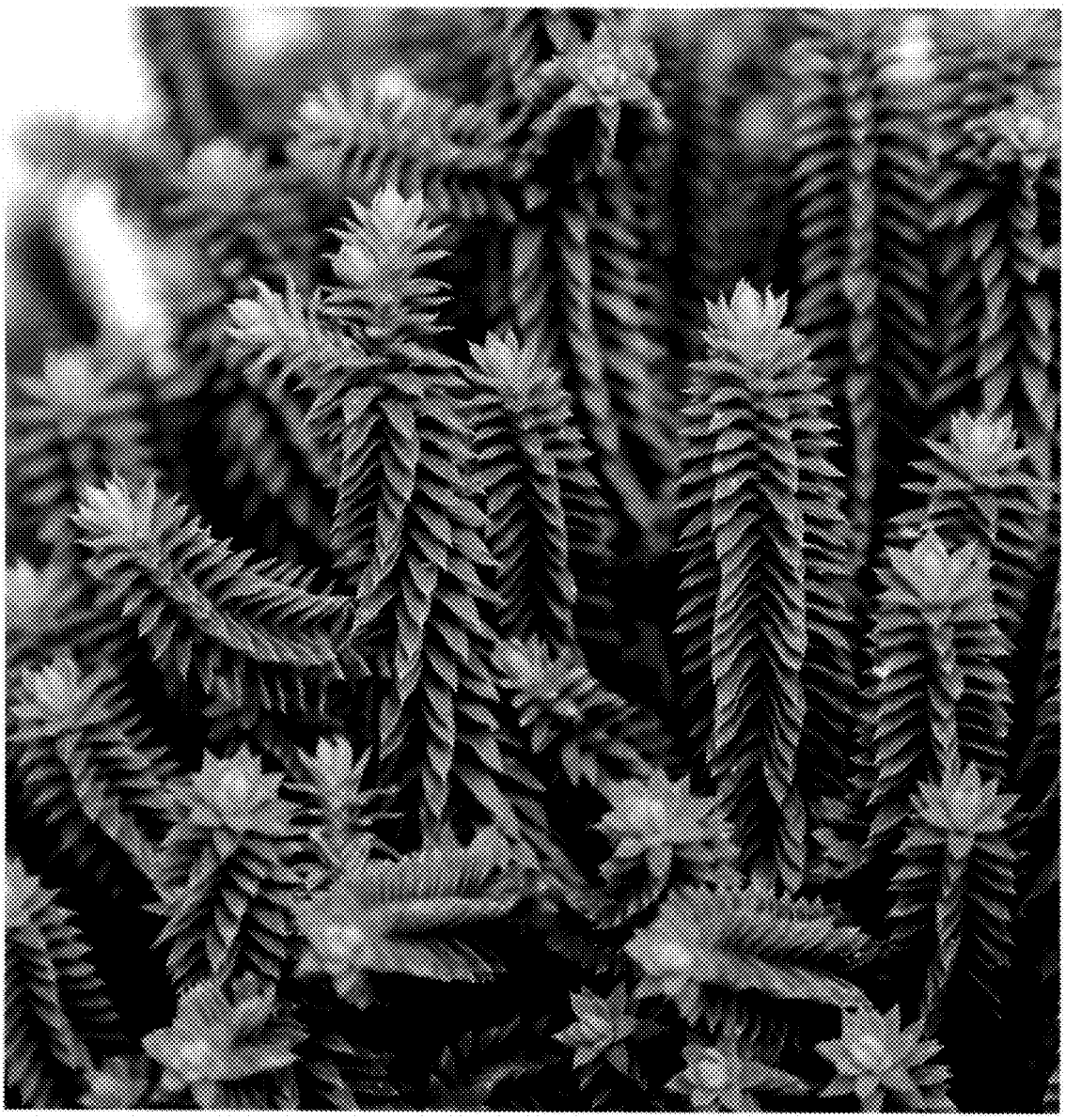

The photograph in FIG. 2 provides a provides a close-up view of the foliage of 'El Paso'.

The colors in the photograph are as close as possible with the photographic and printing technology utilized and the values cited in the detailed botanical description accurately describe the colors of the new cultivar.

DETAILED BOTANICAL DESCRIPTION

The following is a detailed description of plants of the new cultivar 36 months in age as grown in 15-cm containers in an unheated greenhouse in Wezep, The Netherlands. The phenotype of the new cultivar may vary with variations in environmental, climatic, and cultural conditions, as it has not been tested under all possible environmental conditions. The color determination is in accordance with The 2015 (2019 reprint) Colour Chart of The Royal Horticultural Society, London, England, except where general color terms of ordinary dictionary significance are used.

General description:

*Plant type*.—Evergreen coniferous shrub.

*Plant habit*.—Compact and globular.

*Height and spread*.—An average of 25 cm in height and width as a 3-year-old plant grown in a container.

*Cold hardiness*.—At least to U.S.D.A. Zone 6.

*Diseases and pests*.—No susceptibility or resistant to pests and diseases has been observed.

*Root description*.—Fibrous.

*Root development*.—Time for root initiation is an average of 7 weeks from softwood cuttings, time to produce a fully rooted cutting is an average of 8 months.

*Propagation*.—Softwood stem cuttings.

Branch description:

*Branch shape*.—Rounded.

*Branch size*.—11.4 cm in length and 2 mm in diameter.

*Branch surface*.—Covered with scale-like leaves, matte.

*Branch strength*.—Strong.

*Branching*.—Per plant; main 9, lateral 50.

*Branch arrangement*.—Alternate.

*Branch aspect*.—Average angle of 25° to vertical.

*Internode length*.—2.1 cm in length.

*Branch color*.—Young stems; N144D, mature stems; 177B, older wood and bark; N199B and N199C, internodes; young N144C, mature N199C.

Foliage description:

*Leaf arrangement*.—Opposite, whorls of 3.

*Leaf shape*.—Lanceolate to linear, carinate.

*Leaf division*.—Single.

*Leaf base*.—Decurrent.

*Leaf apex*.—Apiculate, leaf apices are soft and not sharp to the touch.

*Leaf venation*.—Not visible.

*Leaf margins*.—Entire.

*Leaf surface*.—Upper surface; slightly glabrous, lower surface; matte.

*Leaf color*.—Young upper surface; 144A, base 144C, young lower surface; 144A, apex and base 144C, mature upper surface; 141A and 143A, mature; lower surface; 144A, 2 parallel stomatal lines 190D, fall; a blend of 177D and 182C on both surfaces.

*Leaf aspect*.—Held in an average angle of 112.5° (slightly downward of 90° to lateral branch).

*Leaf fragrance*.—Moderate fragrance when crushed, cedar-like, typical for *Chamaecyparis*.

*Leaf size*.—An average of 6 mm in length and 1.5 mm in width.

*Leaf quantity*.—An average of 380 scale-like leaves per branch.

Cone description: No flowers or cones observed to date.

It is claimed:

1. A new and distinct cultivar of *Chamaecyparis* plant named 'El Paso' substantially as herein illustrated and described.

* * * * *